United States Patent
Han et al.

(10) Patent No.: US 12,181,393 B2
(45) Date of Patent: Dec. 31, 2024

(54) ELECTROKINETIC-BASED CONCENTRATOR DEVICE AND METHOD

(71) Applicant: Massachusetts Institute of Technology, Cambridge, MA (US)

(72) Inventors: Jongyoon Han, Bedford, MA (US); Hyuckjin Kwon, Somerville, MA (US)

( * ) Notice: Subject to any disclaimer, the term of this patent is extended or adjusted under 35 U.S.C. 154(b) by 899 days.

(21) Appl. No.: 17/191,842

(22) Filed: Mar. 4, 2021

(65) Prior Publication Data

US 2021/0346844 A1    Nov. 11, 2021

Related U.S. Application Data

(60) Provisional application No. 63/020,205, filed on May 5, 2020.

(51) Int. Cl.
| | | |
|---|---|---|
| *G01N 1/40* | (2006.01) | |
| *B01D 57/02* | (2006.01) | |
| *B01D 61/02* | (2006.01) | |
| *B01D 61/48* | (2006.01) | |
| *G01N 33/487* | (2006.01) | |

(52) U.S. Cl.
CPC ............ *G01N 1/40* (2013.01); *B01D 57/02* (2013.01); *B01D 61/027* (2013.01); *B01D 61/485* (2013.01); *G01N 33/48707* (2013.01); *B01D 2325/0282* (2022.08); *G01N 2001/4038* (2013.01); *G01N 2800/26* (2013.01)

(58) Field of Classification Search
CPC .......... B01D 2313/025; B01D 2313/04; B01D 2325/0282; B01D 61/027; B01D 61/485; B01D 61/464; B01D 61/46; B01D 57/02; G01N 1/40; G01N 2001/4038; B01L 2300/0645
USPC ........................................................ 204/550
See application file for complete search history.

(56) References Cited

U.S. PATENT DOCUMENTS

| | | | | |
|---|---|---|---|---|
| 6,972,080 | B1 * | 12/2005 | Tomioka ................ | C12M 47/02 204/600 |
| 8,062,485 | B2 * | 11/2011 | Ogawa ..................... | C02F 1/48 204/276 |
| 9,725,340 | B2 * | 8/2017 | Kim ........................ | C02F 1/469 |
| 9,845,252 | B2 | 12/2017 | Kwak | |
| 10,287,184 | B2 * | 5/2019 | Awad ...................... | C02F 1/004 |
| 11,131,608 | B2 * | 9/2021 | Shkolnikov ........... | B01D 61/38 |
| 2006/0180469 | A1 | 8/2006 | Han et al. | |
| 2018/0319681 | A1 * | 11/2018 | Jo ......................... | C02F 1/4698 |
| 2018/0371400 | A1 | 12/2018 | Kim et al. | |
| 2021/0214247 | A1 * | 7/2021 | Takagi .................. | C02F 1/4602 |
| 2022/0280943 | A1 * | 9/2022 | Webb ..................... | C12M 47/04 |

OTHER PUBLICATIONS

Hach "EZ Arsenic For test kit 2822800 (EZ Arsenic)" 2006 (Year: 2006).*
Kwon et al. "A multiscale-pore ion exchange membrane for better energy efficiency" J. Mater. Chem. A, 2018, 6, 7714 (Year: 2018).*
(Continued)

*Primary Examiner* — Maris R Kessel
*Assistant Examiner* — Alexander R. Parent
(74) *Attorney, Agent, or Firm* — Modern Times Legal; Robert J. Sayre

(57) ABSTRACT

The invention is directed to a scalable concentration device and method of use thereof based on electrokinetics.

33 Claims, 9 Drawing Sheets

(56) References Cited

OTHER PUBLICATIONS

Sung, J. et al., "Nanofluidic concentration devices for biomolecules utilizing ion concentration polarization: theory, fabrication, and applications", Chem. Soc. Rev., 39(3), DOI: 10.1039/b822556g, Jan. 1, 2010, 912-919.
Cashdollar, J. et al., "Methods for primary concentration of viruses from water samples: A review and meta-analysis of recent studies", J. Appl. Microbiol., vol. 115, 2013, 1-11.
Fout, G. et al., "EPA Method 1615. Measurement of enterovirus and norovirus occurrence in water by culture and RT-qPCR. I. Collection of virus samples", J. Vis. Exp., doi:10.3791/52067, 2015, 1-7.
Inglis, T. et al., "Rapid antimicrobial susceptibility tests for sepsis; the road ahead", J. Med. Microbiol., vol. 68, No. 7, 2019, 973-977.
Kwak, R. et al., "Continuous-flow biomolecule and cell concentrator by ion concentration polarization", Anal. Chem., vol. 83, 2011, 7348-7355.
Kwon, H. et al., "A multiscale-pore ion exchange membrane for better energy efficiency", J. Mater. Chem., A 6, 2018, 7714-7723.
Ouyang, W. et al., "Pressure-Modulated Selective Electrokinetic Trapping for Direct Enrichment, Purification, and Detection of Nucleic Acids in Human Serum", Anal. Chem., vol. 90, 2018, 11366-11375.
Pham, S. et al., "Helical vortex formation in three-dimensional electrochemical systems with ion-selective membranes", Phys. Rev., E 93, 033114, 2016.
Wang, Y. et al., "Million-fold preconcentration of proteins and peptides by nanofluidic filter", Anal. Chem., vol. 77, 2005, 4293-4299.

\* cited by examiner

ELECTROKINETIC-BASED CONCENTRATOR DEVICE AND METHOD

RELATED APPLICATION

This application claims the benefit of U.S. Provisional Application No. 63/020,205 filed May 5, 2020. The entire teachings of the above-referenced application are incorporated herein by reference.

GOVERNMENT SUPPORT

This invention was made with Government support under Grant No. R01 AI117043 awarded by the National Institutes of Health (NIH). The Government has certain rights in the invention.

BACKGROUND OF THE INVENTION

An electrokinetic concentrator device which operates based on electrokinetic force-based separation has been previously described and comprises a combination of a microchannel and a nanochannel (see, e.g., Wang, Y.-C et al. Million-fold preconcentration of proteins and peptides by nanofluidic filter. *Anal. Chem.* 77, 4293-9 (2005); U.S. Pat. App. Pub. No. 20060180469). The underlying mechanism is the coupling of electrokinetic and drag forces which enables charge-based separation. This is in contrast to concentration methods which use a conventional filter in which size separation is accomplished mainly by the sieving mechanism [1]. Without any physical filter, electrokinetic-based separation techniques can separate various bio-molecules such as a nucleic acid from a buffer or sample fluid and concentrate bio-molecules rapidly with a maximum concentration factor of over $10^6$ [2, 3].

Electrokinetic force-based separation techniques have been intensively studied. Despite the tremendous interest and advantages of such electrokinetic-based separation techniques, such systems and methods have thus far been limited to the microfluidic scale. For example, when the channel is larger than microscale, 3D-helical vortices are induced thus limiting the separation efficiency [4].

There remains a need in the art for electrokinetic concentrator devices and methods that are scalable, can be utilized under high flux, and/or capable of detecting low abundance biomolecules.

SUMMARY OF THE INVENTION

The present invention is directed to a scalable concentration device and method of use thereof based on electrokinetics. These devices can be contrasted with devices and methods that utilize conventional filters based on a sieving mechanism. The proposed electrokinetic concentrator can, for example, concentrate bacteria selectively from blood without the clogging issue which is associated with the use of conventional filters. The devices and methods described herein can also encompass the use of beads to produce a stable electric field by geometrical confining and enable cell lysis of concentrated bacteria by a bead beating mechanism for downstream assay of the lysate. The device and methods can be used, for example, for the detection of low abundance biomolecules; for example, the device and method can be used for diagnosis of sepsis by concentrating and detecting bacteria in a blood sample.

In certain embodiments, the invention is directed to an electrokinetic concentrating device comprising:
i) an anode chamber comprising an anode and a buffer solution;
ii) a cathode chamber comprising a cathode and a buffer solution;
iii) a main chamber disposed between the anode chamber and the cathode chamber and separated therefrom, wherein the main chamber further comprises a first CEM on the anodic side of the main chamber and a second CEM on the cathodic side of the main chamber, wherein the second CEM is a multi-scale porous cation exchange membrane (a MP-CEM), and wherein the first CEM and the second CEM are configured in the main chamber such that a sample fluid flows across the first CEM and then across the second CEM;
iv) a microporous structure disposed on or in proximity to the second CEM, wherein the microporous structure suppresses electroconvection; for example, has dimensions sufficient to suppress electroconvection; and
v) an inlet conduit in fluid communication with the anodic side of the main chamber;
wherein the anode and the cathode are configured to induce an electric field in the main chamber;
wherein the MP-CEM comprises nanopores and micropores;
wherein the second CEM has a top side and a bottom side, wherein the top side faces the anode and the bottom side faces the cathode;
wherein the microporous structure is disposed on or in proximity to the top side of the second CEM and stabilizes the ion-depleted region on the second CEM.

In certain aspects, the first CEM is a conventional CEM comprising only nanopores and does not comprise micropores. In other aspects, the first CEM is an MP-CEM (comprising nanopores and micropores).

The sample fluid comprises particles to be concentrated. As described in more detail below, the particles in the sample fluid are concentrated at the microporous structure due to operation of the device. The microporous structure can, for example, comprise a structure comprising fibers (e.g., comprising cotton fibers or a cotton ball) or can be a plurality of beads.

The invention also encompasses a method for concentrating particles from a sample fluid, the method comprising introducing the sample fluid into the concentrator device described herein via the inlet conduit, inducing an electric field across the main chamber, and causing the sample fluid to flow first across the first CEM and then across the second CEM, wherein negatively charged particles are concentrated at the microporous structure. The particles can, for example, be negatively charged particles. In additional aspects, the particles are cells such as bacterial cells. The sample fluid can be a biological fluid, including, but not limited to, blood. The methods described herein can be used for the detection of low abundance bacteria or low abundance virus in a biological sample, for diagnosing disease (such as sepsis and meningitis), for detecting a waterborne pathogen, and/or for monitoring food safety.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale emphasis instead being placed upon illustrating the principles of the invention.

FIG. 1A is a schematic of electrokinetic concentration without the microporous structure. The hemispherical-shaped ion-depleted regions are formed resulting in poor accumulation efficiency because the direction of electrophoretic and drag velocities are not parallel and equal. FIGS. 1B-1D show fluorescence microscopic images for the electrokinetic filter which is capturing the fluorescence dye (green) without the microstructure. FIG. 1F is a schematic of an ion-depleted region stabilized by the microstructure. The accumulation plug is well-formed because the electrophoretic and drag velocity are the same but exerted in opposite directions. FIGS. 1G-1I show fluorescence microscopic images of well-formed accumulation plug.

FIGS. 2A and 2E shows a schematic of the electrokinetic concentrator consisting of electrodes, CEM, MP-CEM, the fibrous microporous structure (e.g., a cotton ball), and an inlet tube. FIGS. 2B and 2F is a three-dimensional rendering image of the device showing the three separated chambers: the anode buffer chamber, the cathode buffer chamber, and the main chamber. FIGS. 2C and 2G is a schematic of the MP-CEM, which allows for electrokinetic force and fluid transport. Only cation transport occurs between the main and buffer chambers because of the unique compressed structure of the MP-CEM which is sandwiched between two silicone rubber blocks or silicone gaskets. The compression of the MP-CEM results in removal of the micropores. Because of the compressed structure of the MP-CEM, the border between electrode chamber and the main chamber is compressed to eliminate the micro-pores mechanically (but nano-pores remain present). FIGS. 2D and 2H are photographs of the electrokinetic concentrator.

FIGS. 4A-4E shows a selective bacteria (GFP E. coli) concentration experiment. FIG. 4A-4B show the mechanism and experimental setup of selective bacteria concentration from the blood. Most of the hemoglobin penetrates the electrokinetic concentrator whereas most of the E. coli is captured by the electrokinetic concentrator. FIGS. 4D-4F are the images of microfiber with different flow rates of 10 ml diluted blood (1/10×) showing the concentrated hemoglobin move downward, by increasing flow rate from 0.2 mL/min (FIG. 4D) and 0.3 ml/min (FIG. 4E). Eventually, at 0.5 mL/min (FIG. 4F), hemoglobin is not concentrated to avoid any clogging. FIGS. 4G-4I are image of the input, concentrated and filtrate streams, respectively. FIG. 4J is a fluorescence image of the input stream. FIG. 4K is a fluorescence image of a concentrated stream showing a more fluorescence dots from E. coli than the input due to the concentration. FIG. 4L shows the filtrate stream which is completely dark due to the absence of E. coli.

FIG. 6A is a fluorescence microscopy image of the inlet stream: the GFP E. coli are shown as bright dots. FIG. 6B is an image of a concentrated stream indicating 85.34% of recovery ratio (as measured by hemocytometer). FIG. 6C is an image of the outlet stream showing 99.12% of filtration rate. FIG. 6D is an image after performing bead beating showing good lysis performance.

FIG. 9A shows a large volume of a sample containing low abundant target loaded into the proposed electrokinetic concentrator. FIG. 9B shows that bio-molecules from the sample are concentrated at the fibrous microporous structure. FIG. 9C shows that the concentrated target migrates to the downstream ICG sensor. FIG. 9D shows that the ICG sensor displays the result by color change.

DETAILED DESCRIPTION OF THE INVENTION

Figures 1A, 1B, 1C, 1D, 1E, 1F, 1G, 1H, 1I:
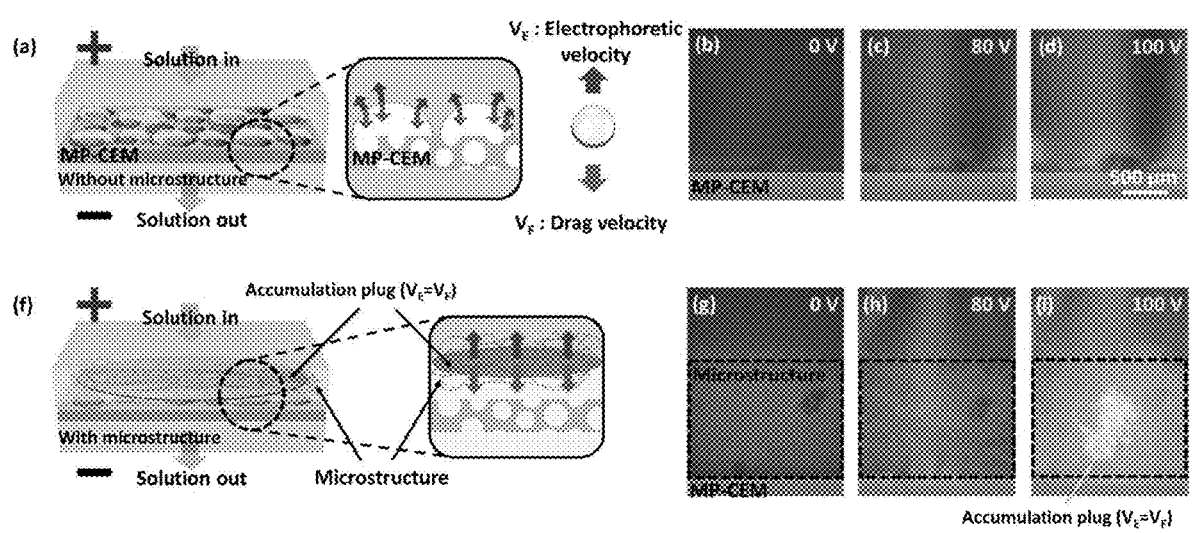
FIGS. 1A-1I demonstrate a key mechanism of the electrokinetic concentrator. A particle, such as a bacterial cell, is stopped where the electrophoretic velocity ($V_E$) and drag velocity ($V_F$) are canceled out.
Figures 2A, 2B, 2C, 2D, 2E, 2F, 2G, 2H:
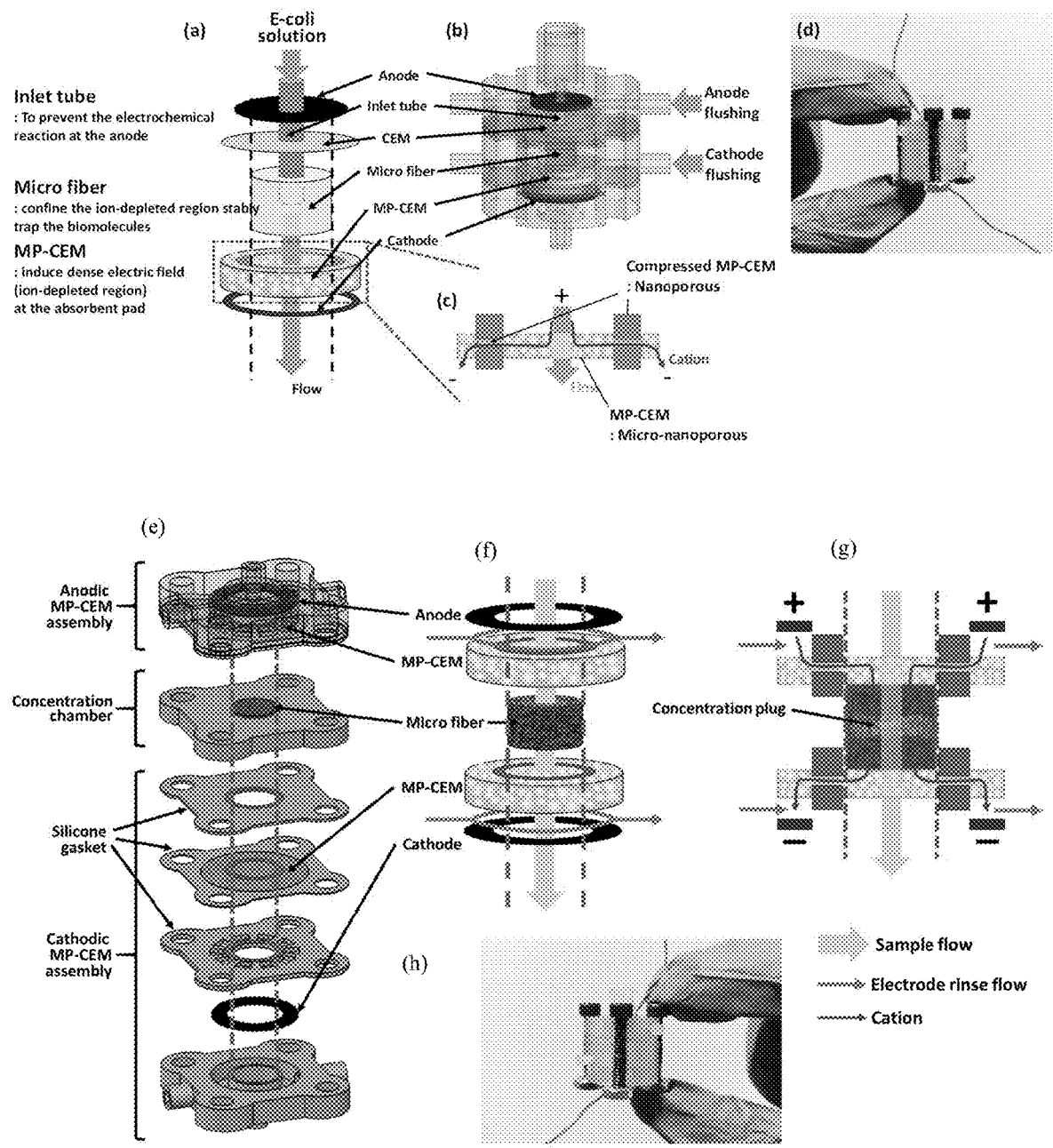
FIGS. 2A-2H show a configuration of the electrokinetic concentration device.

A description of preferred embodiments of the invention follows.

As used herein, the words "a" and "an" are meant to include one or more unless otherwise specified. For example, the term "a cell" encompasses both a single cell and a combination of two or more cells.

The term "particle" and "particles" includes, but is not limited to, cells, beads, viruses, organelles, nanoparticles, and molecular complexes. The term "particle" or "particles"

can include a single cell and a plurality of cells. Cells can include, but are not limited to, bacterial cells, blood cells, sperm cells, cancer cells, tumor cells, mammalian cells, protists, plant cells, and fungal cells.

A "patient" or "subject" is an animal to be treated or diagnosed or in need of treatment or diagnosis, and/or from whom a biofluid is obtained. The terms "patient" and "subject" includes humans.

The term "electrokinetic" refers to the electrically driven motion of charged particles or fluid. Electrokinetic flow is the movement of fluid or fluid borne material under an applied electric field. Electrokinetic flow generally encompasses one or both of electrophoresis, e.g., the movement of charged species through the medium or fluid in which it is disposed, as well as electroosmosis, e.g., the electrically driven movement of the bulk fluid, including all of its components. Accordingly, it will be appreciated that what is envisioned is the full spectrum of electrokinetic flow from predominantly or substantially completely electrophoretic movement of species, to predominantly electroosmotically driven movement of material, e.g., in the case of uncharged material, and all of the ranges and ratios of the two types of electrokinetic movement that fall between these extremes.

"Liquid flow" and "fluid flow" encompass any or all of the characteristics of flow of fluid or other material through a passage, conduit, channel or across a surface. Such characteristics include, without limitation, the flow rate, flow volume, the conformation and accompanying dispersion profile of the flowing fluid or other material, as well as other more generalized characteristics of flow, e.g., laminar flow, creeping flow, turbulent flow, etc.

As discussed above, despite the recognized advantages of electrokinetic-based separation techniques, such systems and methods have thus far been limited to the microfluidic scale. When the channel is larger than microscale, 3D-helical vortices are induced thus limiting the separation efficiency [4]. In addition, in many studies, the nanochannel or its assembly, such as ion exchange membrane (IEM), is fabricated and located underneath the microchannel which allows fluid flow to pass through the ion-depleted region to maximize the separation driving force. This is not scalable in three dimensions. In order to overcome this limitation, we have recently developed a unique membrane, termed multiscale porous ion exchange membrane (MP-IEM) which has both nano-pores for ion flow and micro-pores for fluid flow [5,6].

The use of a MP-IEM is a viable approach to actualize the scalable assembly of microchannel and nanochannel combination.

As described above, the inventive device comprises an MP-IEM. The MP-IEM incorporates both nanoporous and microporous structures and thus allows formation of the ion-depleted region as well as fluid transport across the membrane through the micropores. Particles such as bacteria experience mainly two forces under a DC electric field: the electrophoretic force and the drag force. The drag force, induced by hydraulic flow, is exerted in the direction opposite to that of the electrophoretic force. The electrophoretic force is induced by the electric field. FIG. 1A depicts the movement of oil droplets across an MP-IEM. The oil droplets are stopped and concentrated where the electrokinetic velocity or electrokinetic force and drag forces are canceled out.

In order to maximize the driving force of electrokinetic filtering, the applied electric field should be concentrated. The cation exchange membrane (CEM), which has a nanoporous structure, generates an ion-depleted region at the surface of the CEM. The generated ion-depleted region provides resistance for ionic current thus concentrating the intensive electric field and generating an electrokinetic force. Conventional (nanoporous) CEMs only can have a shear directional flow which is perpendicular to the electrophoretic force, therefore the electrophoretic force cannot be canceled out by the drag force. To cancel out the forces completely, the present invention incorporates the cation version of MP-IEM referred to herein as "multiscale porous cation exchange membrane" (MP-CEM), which has both nanoporous and microporous structure, allowing not only the ion-depleted region but also fluid transport across the membrane by micropores, thus generating a drag force in an opposite direction from the electrophoretic force.

Use of an MP-CEM alone in an electrokinetic concentrator does not result in a well-distributed electrokinetic force. As shown in FIG. 1F, electro-convection (3-D helical vortex) is observed with the MP-CEM which results in hemispherical-shaped ion-depleted regions and thus bad filtering efficiency. Generation of an evenly formed ion-depleted region is required to order to achieve higher efficiency. In order to accomplish this, the device described herein comprises a microporous structure located at or in proximity to the top surface of the MP-IEM to suppress the electro-convection by confining to microscale geometries as shown in FIG. 1F. The fluorescence images shown in FIGS. 1B-1D and 1G-1I provide a comparison between the use of the MP-CEM without and with the microstructure. The combination of the MP-CEM and the microporous structure make the device scalable and concentrate the fluorescence dye effectively.

The electrokinetic concentrator described herein has a scalable design. The size of the concentrator can be scaled according to the required flux. The electrokinetic device can consist of three chambers as shown in FIGS. 2A-2H. The anode and cathode chamber can, for example, have Ag/AgCl electrodes, respectively, to apply an electric field. Buffer solution is circulated in order to rinse the electrodes. The main chamber, where the sample solution flows and bacteria is concentrated, can be separated by the CEM and MP-CEM from the anodic and cathodic buffer, respectively, to prevent electrochemical reaction between the electrode and sample solutions thus allowing only cation transport through the CEM and MP-CEM. The main chamber is separated from the anode and cathode chambers when buffer solution cannot enter the main chamber but ion transport between the chambers is permitted. The separation can, for example, be accomplished, at least partially, by compressing the MP-CEM as described herein. In the examples shown in the figures, a cotton ball acts as a fibrous microporous structure and stabilizes the ion-depleted region. Bacteria are concentrated at the cotton ball as shown in FIG. 1I.

A simple mathematical analysis was performed to model the concentration of particles and this analysis can be compared with the experimental results for verification. First, the drag velocity is simply proportional to the flow rate and this relationship can be expressed as follows:

$$V_F = \frac{Q}{A}, \tag{1}$$

where Q is flow rate and A is the cross-sectional area of the channel.

Figure 3:
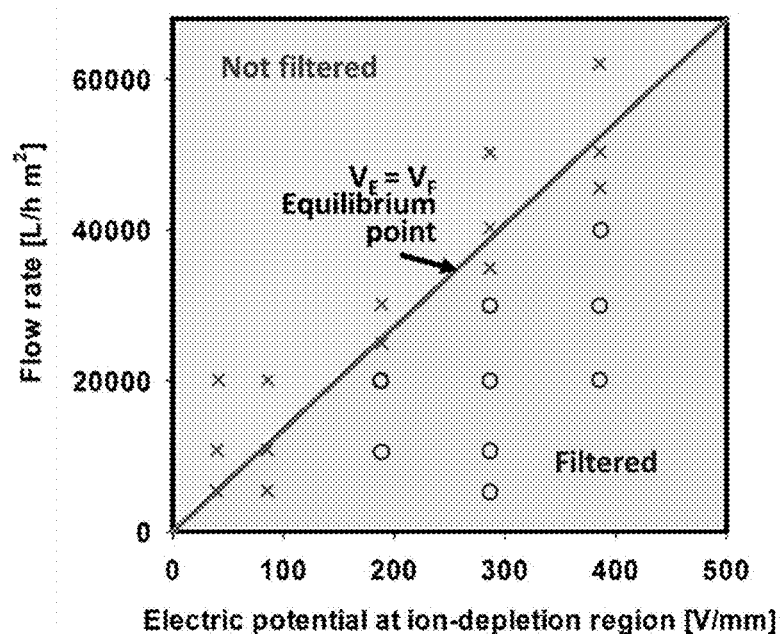
FIG. 3 is a graph comparing the simple mathematical analysis and the experimental results. The pink line indicates the theoretical equilibrium points ($V_E=V_F$) based on the simple mathematical analysis. The upper portion of the graph (to the left of the line: shaded in red) is the "not filtered regime" due to the higher $V_F$ than $V_E$ while the bottom portion of the graph (to the right of the line: shaded in blue) is the "filtered regime" because equilibrium points ($V_E=V_F$) are well-formed. The circle symbols represent the condition of filtered and the cross symbol are the condition of not filtered carried out by experiment showing a good correlation. Note that this experiment is carried out with an oil droplet representing the bacteria.

Second, the electrophoretic velocity can be expressed as follows:

$$V_E = \frac{\varepsilon_O D_E \zeta E}{\mu_E}, \quad (2)$$

where $\mu_E$ is the viscosity of emulsion, $\varepsilon_O$ is the vacuum permittivity, $D_E$ is a dielectric constant of emulsion, $\zeta$ is zeta potential, and E is the electric potential. Every factor except flow rate and electric potential are constant. Therefore, theoretical equilibrium points (VE=VF) can be simply determined by two factors which are the flow rate (Q) and the electric potential (E) at the ion-depleted region. Consequently, a simple linear relationship between the electric potential at the ion-depleted region and flow rate can be found as FIG. 3 depicts as a line (indicated by the arrow). The filtration was tested experimentally with various flow rates and electrical fields at the ion-depleted region. The experimental results are shown in FIG. 3 as a circle or cross symbol. The results in FIG. 3 indicate a good correlation between the flow rate and the electric potential at the ion-depleted region.

The applied voltage across the device is not exactly equal to the applied electric potential at the ion-depleted region due to the potential drop caused by electrodes and bulk fluid, therefore, it is hard to calculate or assume precisely. Therefore, an additional probe can be placed across the ion-depleted region to directly to measure electric potential at the ion-depleted region. The electric potential numbers shown in FIG. 4 were experimentally measured.

Figures 4A, 4B, 4C, 4D, 4E, 4F, 4G, 4H, 4I, 4J, 4K, 4L:
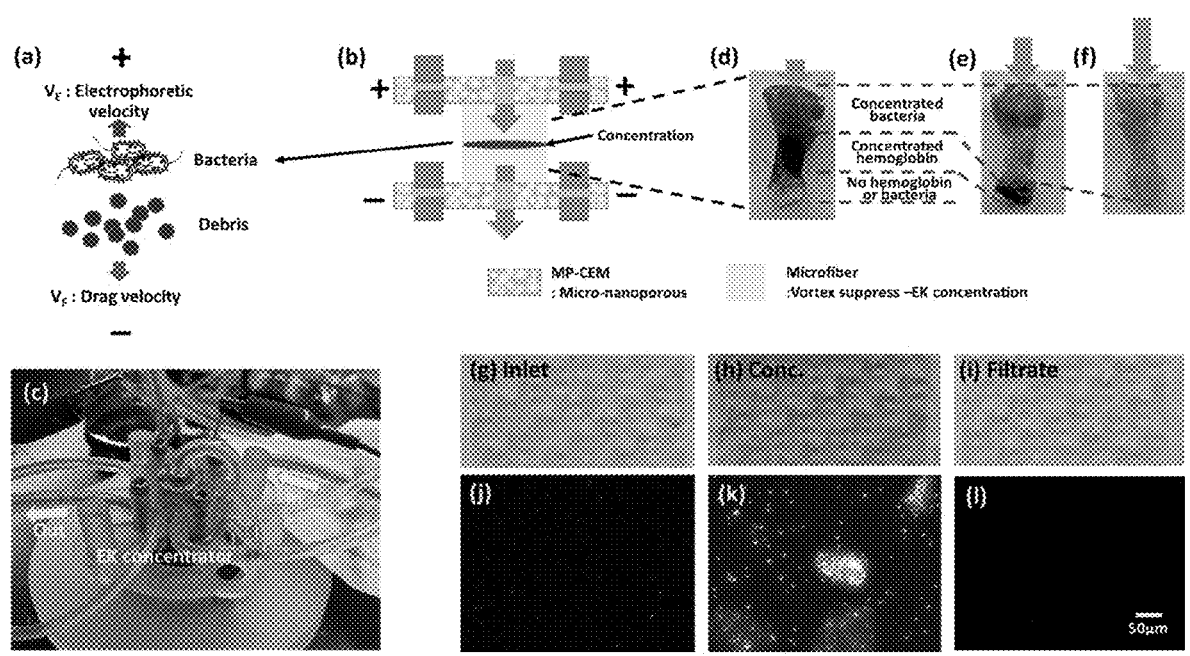

Concentration of bacteria from blood is more challenging than that from clean water because blood includes various components such as red blood cells (RBCs), white blood cells and platelets. If a conventional physical filter for bacterial capture were to be used, it would become clogged immediately with the blood. Although the electrokinetic filter is much better than the conventional filter with respect to the clogging issue, it can still be challenging to capture all the blood components as well as bacteria. Therefore, selective bacteria concentration is necessary in order to concentrate bacteria without clogging. As previously mentioned, the electrokinetic concentrator described herein operates based on charge-based separation thus under certain conditions, more negatively charged particles remain at the top of the electrokinetic filter (the MP-IEM) while less charged particles pass through the electrokinetic filter. Bacteria is generally more negatively charged than other blood components thus allowing for selective concentration of bacteria. FIG. 4 shows the experimental result of selective concentration of bacteria from 1/10× diluted blood. The dilution (with deionized water) of blood resulted in osmotic lysis of RBCs thus forming hemoglobin. With a flow rate of 0.3 ml/min and voltage of 200 V, the hemoglobin passes through the electrokinetic concentrator whereas *E. coli* cannot pass through and the *E. coli* is thereby concentrated at the cotton ball due to the electrophoretic force.

A well-recognized bottleneck in sample preparation is efficient lysis. In order to analyze the DNA, RNA and proteins contained within the cells, for example, by downstream assay such as a PCR or immunochromatography, wall membranes of the cell need to be disrupted to produce a lysate. Bead beating is a process that can be used to disrupt a wide range of the biological samples. In an example of bead beating, sample cells are placed in tubes with appropriate grinding beads and subjected to high energy mixing. The beads impact the sample mechanically, eventually breaking the sample down on the cellular level and causing release of subcellular contents.

In the figures, the zirconium beads having a size (diameter) of 0.1 mm were used for bead beating. Zirconium beads have been widely used for bead beating and have the following characteristics:

High specific gravity which can shorten the grinding time and improve production efficiency;
High strength, high hardness, not easily broken, no peeling;
Good toughness, wear-resistant, do not pollute the grinding materials, good roundness;
Low binding.

Figure 5:
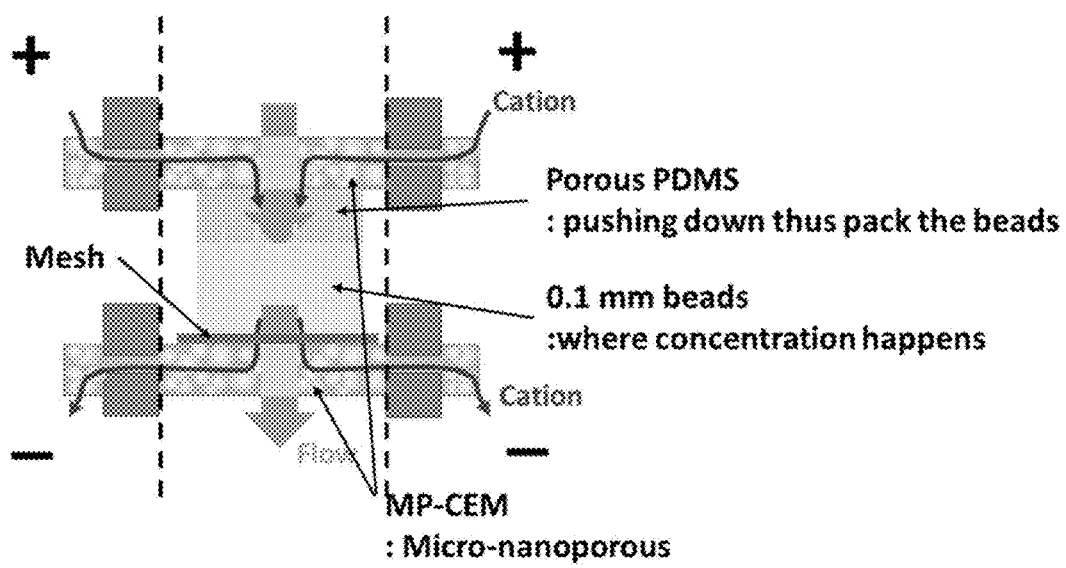
FIG. 5 is a schematic of bead beating integration. The 0.1 mm zirconium beads are completely packed by the porous PDMS and a mesh in the main chamber forming a homogenous microporous structure that stabilizes the ion-depleted region thus inducing an evenly distributed electrokinetic force. When strong mixing is applied, the elastic properties of porous PDMS provides enough space for bead movement for efficient bead beating.

FIG. 5 is a schematic showing bead beating integration. To integrate bead beating with the electrokinetic concentrator, a porous PDMS block and a mesh was used to pack the beads in the main chamber. Similar to a cotton ball described above, packed beads can also act as the homogenous microporous structure that stabilizes the ion-depleted region inducing a well distributed electrokinetic force thus forming a stable concentration plug.

The porous PDMS block plays an important role in bead beating and also pushes down the beads to provide packing. Because the porous PDMS has elastic property, it also allows enough space for the movement of the beads while enabling the bead beating when the strong mixing is applied to the device.

The porosity created by beads can be easily calculated. In geometry, the density of closely-packed equal spheres is 0.7405. Therefore, the porosity created by beads is about 26%, which is much smaller than a cotton ball, for example. The drag velocity as determined by flow velocity determines the flux performance of the device. Consequently, when the cotton ball is replaced by beads, the area of the horizontal cross-section would need to be proportionally increased to keep the same flux as that with the cotton ball. In order to accomplish this, an MP-CEM (replacing the upper conventional CEM) was adopted to provide a largely well-distributed inlet stream. In like manner to the lower MP-CEM, the upper MP-CEM is also squeezed or compressed (e.g., by silicone rubber blocks or other structures) to separate the buffer chamber and the main chamber allowing only cation transport.

Figures 6A, 6B, 6C, 6D:
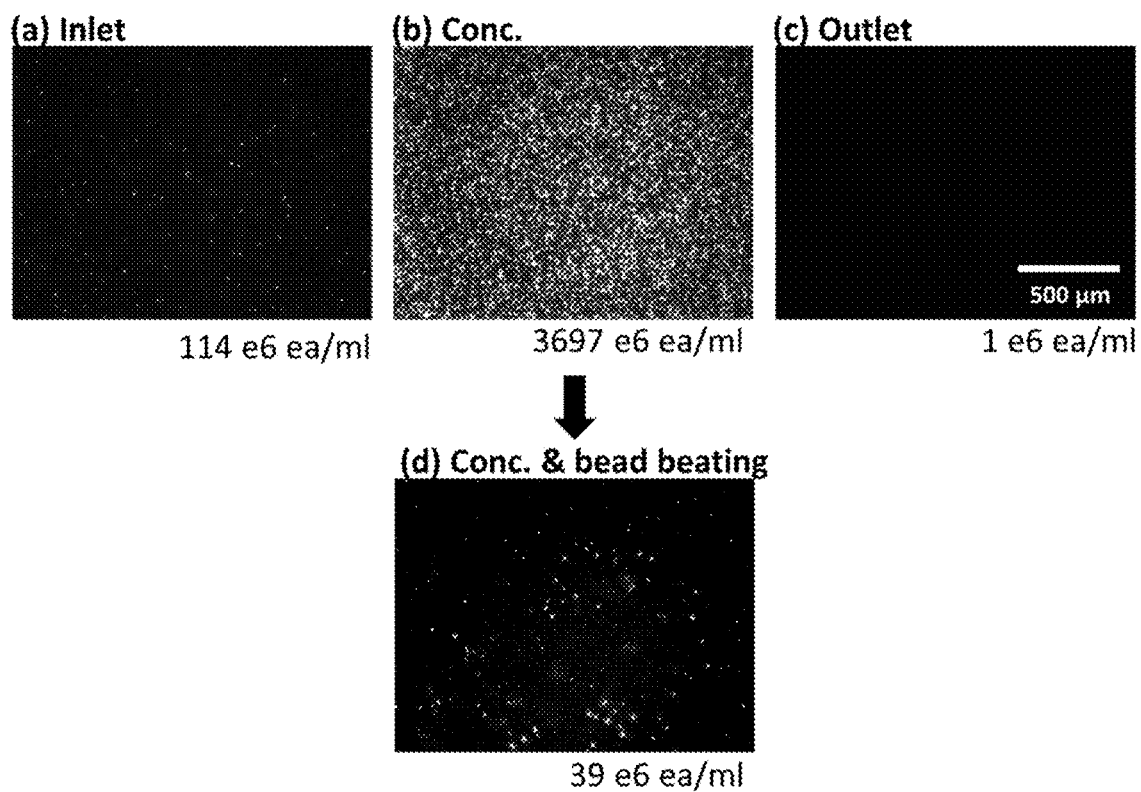
FIGS. 6A-6D show the concentration and lysis performance evaluation of integrated bead beating.

To verify the effectiveness of bead beating integration, we investigated the performance of lysis as well as concentration. As shown in FIG. 6, 3 ml of GFP *E. coli* solution was successfully concentrated into 77 μl with a flow rate of 1 ml/min under 200 V, showing good concentration performance. The bead beating performance was also investigated as shown in FIG. 6D showing the concentrated *E. coli* cells are almost lysed under the applied vortex (2500 rpm, 5 minutes) by induced bead beating.

As discussed above, the invention encompasses an electrokinetic concentrating device and methods of use thereof. The electrokinetic concentrating device comprises:

i) an anode chamber comprising an anode and a buffer solution;
ii) a cathode chamber comprising a cathode and a buffer solution;
iii) a main chamber disposed between the anode chamber and the cathode chamber and separated therefrom, wherein the main chamber further comprises a first CEM on the anodic side of the main chamber and a second CEM on the cathodic side of the main chamber, wherein the second CEM is a MP-CEM, and wherein the first CEM and the second CEM are configured in the main chamber such that a sample fluid flows across the first CEM and then across the second CEM;

iv) a microporous structure disposed on or in proximity to the second CEM, wherein the microporous structure has dimensions sufficient to suppress electroconvection; and v) an inlet conduit in fluid communication with the anodic side of the main chamber;

wherein the anode and the cathode induce an electric field in the main chamber; wherein the MP-CEM comprises nanopores and micropores; wherein the second CEM has a top side and a bottom side, wherein the top side faces the anode and the bottom side faces the cathode; and wherein the microporous structure is disposed on or in proximity to the top side of the second CEM and stabilizes the ion-depleted region on the second CEM.

Various fluids comprising mixtures of particles, including negatively charged particles, can be used as the sample fluid in the device and methods described herein. Examples of sample fluids include biological fluids or biofluids (e.g., a biological sample such as blood, lymph, serum, urine, mucus, sputum, cervical fluid, placental fluid, semen, spinal fluid, and fluid biopsy), liquids (e.g., water), food samples, water samples, culture media, emulsions, sewage, fluid from a biomanufacturing process, etc. In embodiments in which the biofluid is whole blood, the blood can be introduced unadulterated or adulterated (e.g., lysed or diluted). Other biological fluids or biofluids can also be used unadulterated or adulterated (e.g., the biofluid can be pre-treated in some way or diluted). Similarly, other fluids can also be used unadulterated or adulterated.

The main chamber comprises the first CEM and the second CEM as well the microporous structure. Sample fluid is introduced into the main chamber via the inlet conduit and particles in the sample fluid are concentrated within the main chamber. The main chamber is separated from the anode and cathode chambers such that the buffer solution of the anode and cathode chambers cannot enter the main chamber. Only ions (cations, in the case of CEMs) are transported from an electrode chamber to the main chamber. The inlet conduit comprises an inlet into which sample fluid can be introduced and a conduit which directs the sample fluid to the anodic side of main chamber such that the sample fluid flows across the first CEM and then across the second CEM.

The dimensions of the main chamber are scalable and can be adapted based on the intended use, flow rate, characteristics of the sample fluid, etc. The microstructure can, in some embodiments, have the same height and/or diameter as the main chamber. In other aspects, the microstructure can have a dimension (height and/or diameter) that are smaller than that of the main chamber. In exemplary aspects, the height of the main chamber is between about 2 mm and about 10 mm, and/or the diameter of the main chamber is between about 4 mm and about 15 mm. In additional exemplary embodiments, the height of the microporous structure is between about 2 mm and about 10 mm, and/or the diameter of the microporous structure is between about 4 mm and about 15 mm.

The sample fluid can comprise particles that are concentrated at the microporous structure. Concentration "at" the microporous structure is intended to encompass concentration on the surface of the microporous structure and/or within the microporous structure. As shown in the figures, the concentration plug can be formed within the microporous structure. The particles can, for example, be cells. In certain aspects, the particles are bacterial cells. When the device comprises CEMs, the particles can be negative charged particles.

The electrokinetic concentrator devices and methods described herein comprise ion exchange membranes (IEMs) that act as ion filters by allowing only cations or anions to pass through. The term "ion exchange membrane" encompasses cation and anionic exchange membranes. A cation exchange membrane can be referred to as a CEM. Strong anion or cation exchange membranes, as those products are generally sold in the art, can be used. NAFION™ membranes, FUMASEP® FTAM-E and FTCM-E (FuMATech CmbH, Germany) are suitable membranes. However, others can also be used. In particular, the term "ion exchange membrane" is intended to include not only porous, microporous or nanoporous films, but also resins or materials through which ions can pass. In some embodiments, an ion exchange resin can be entrapped by one or more meshes (or porous membranes) in lieu of or in addition to one or more of the ion exchange membranes. The term "ion exchange membrane," "cation exchange membrane," "IEM" and "CEM" encompasses such membranes which comprise only nano-sized pores (nanopores) as well as membranes which comprising nano-sized and micron-sized pores (micropores). As discussed in more detail below, an IEM or CEM which comprises nanopores and micropores can be referred to as a multi-scale porous ion exchange membrane (MP-IEM) or a multi-scale porous cation exchange membrane (MP-CEM). MP-IEMs have been described for example in Kwon, H. J., Kim, B., Lim, G. & Han, J. A multiscale-pore ion exchange membrane for better energy efficiency. *J. Mater. Chem. A* 6, 7714-7723 (2018); the contents of which are expressly incorporated by reference herein.

In certain aspects, the first CEM can be a conventional CEM that does not comprise micropores; thus, the first CEM can be a cation exchange membrane comprising only nanopores. In yet other aspects, both the first and the second CEMs are MP-CEMs. The diameter of the micropores of the MP-CEM can, for example, be from about 50 to about 300 um. The diameter of the nanopores of the CEMs are small enough to only permit the transport of ions; for example, be less than about 0.02 μm.

The electric field in the main chamber is created by the anode and the cathode. The anode and cathode chambers are filled with a buffer solution, for example, phosphate buffered saline (PBS). Alternating current (AC), direct current (DC), or both types of fields can be applied. The electrodes can be made of almost any metal. In some embodiments, the anode and cathode are Ag/AgCl electrodes, respectively. In certain aspects, the voltage applied is between 10 V and 500 V.

As discussed above, the first CEM and the second CEM are arranged in the main chamber such that fluid flows from the inlet conduit into the main chamber and across the first CEM before flowing across the second CEM. Fluid flow is in the direction from the anode to the cathode; thus, the inlet conduit is in fluid communication with the anodic side of the main chamber. The first CEM can, for example, be located on the anodic side of the main chamber (the side of the main chamber closer to the anode) while the second CEM is located on the cathodic side of the main chamber (the side of the main chamber closer to the cathode). The one or more MP-CEMs can be compressed so as to separate the main chamber from the buffer chamber(s). As used herein, the MP-CEM is compressed when at least part or all of the portion of the MP-CEM that would otherwise be in fluid contact with the buffer solution(s) is compressed or squeezed such that the micropores are eliminated but the nanopores are maintained. As illustrated in the figures, the MP-CEM can for example be compressed by and between two structures, (which can be the same or different; for example, the structures can be silicone rubber structures) thus only permitting cation transport from the buffer chambers.

The microporous structure can be a single structure that has micron-sized pores (for example, a cotton ball or other fibrous structures) or comprises a plurality of structures (for example, a plurality of beads) that together (e.g., when packed) form micron-sized pores. The microporous structure is disposed or located on or in proximity to the surface of the second CEM (the MP-CEM). A microporous structure "in proximity to" the surface of the second CEM is sufficiently close to the second CEM to suppress electroconvection as described herein. A microporous structure is located "on" the surface of the second CEM when at least a portion of the microporous structure is in physical contact with the second CEM. The microporous structure can be of any suitable material, for example, the microporous structure can comprise fibers, paper, or can be a plurality of beads as described further herein. The fibers of the microporous structure can be natural fibers (e.g., cotton, silk, wool or linen), synthetic fibers (e.g., nylon or polyester or microfiber) and/or regenerated fibers. The microporous structure is scalable, e.g., based on the flow rate and/or dimensions of the main chamber and/or the characteristics of the sample fluid and/or the intended use of the device. The microporous structure has pore dimensions sufficient to suppress electroconvection or stabilize the ion-depleted region on the second CEM. When the microporous structure is a single structure, the microporous structure can have pore dimensions sufficient to suppress electroconvection or stabilize the ion-depleted region when its pore size/diameter, for example, is less than about 100 um. In certain aspects, the height of the microporous structure is greater than about 0.1 mm, greater than about 0.25 mm, greater than about 0.5 mm or greater than about 1 mm. The "height" of the microporous structure refers to the dimension measured from the portion of the microporous structure closest to (or on) the surface of the second CEM (the MP-CEM) to the top or the highest point of the microporous structure.

As discussed above, a plurality of beads can act as the microporous structure (e.g., the beads together form a structure that has pores). The plurality of beads can comprise beads having a diameter that permits bead beating and/or cell lysis; for example, between about 50 and about 400 mm; between about 50 and 300 mm; between about 50 and 200 mm. In certain aspects, the plurality of beads comprises beads having a diameter of a bead is about 100 um. When a plurality of beads are used, the horizontal cross-sectional area of the main chamber needs to be large enough to maintain sufficient flow rate. The desired flow rate will depend on a number of factors, including the characteristics of the sample fluid and/or the type of concentration method and/or the characteristics of the sample fluid In certain aspects, the plurality of beads is part of a bead beating system. A bead beating system is a plurality of beads having dimensions and packing sufficient to lyse cells in the sample fluid upon application of sufficient agitation, such as by stirring or shaking. Lysis is the disruption of the cell membrane and is a standard process for accessing intracellular contents such as nucleic acids, proteins, metabolites, and other organelles. In particular, the extracted biomolecules (for example, nucleic acids and/or proteins and/or virus particles and/or bacteria) from mammalian or microbial cells provide essential information about genetic or disease characteristics. Thus, cell lysis is the first procedure for various biological and clinical studies, including genomics, proteomics and metabolomics, with a wide range of applications in medicine and pharmacy, water-food-energy industry, agriculture, and for recovering of valuable intracellular products from recombinant cells. Bead beating entails mechanical disruption using a plurality of small beads wherein cells and beads are mixed together and the mixture is subjected to a high degree of agitation, for example, by stirring or shaking. Stirring or shaking can be accomplished by hand or using an automatic vibrator. As the cells collide with the beads, the cells are broken open releasing their intracellular contents and thus forming a lysate. The bead beating system of the present invention is used to lyse cells concentrated from the sample fluid at the microporous structure. The beads can be made from any material which can be used for bead beating and/or cell lysis; for example, silica, polystyrene zirconium, glass, ceramics, or stainless steel. In certain aspects, the beads are zirconium beads. The plurality of beads can, for example, be packed in the main chamber between the first CEM and the second CEM. In certain aspects, the plurality of beads are packed in the main chamber between a porous membrane (for example, porous PDMS) and a mesh. The porous membrane can have sufficient elasticity to enable bead beating. The beads can be packed such that their porosity (bead volume divided by total chamber volume) is between about 10 and about 40% or between about 20 to about 30%. In certain aspects, the microporous structure is a bead beating system and the first CEM is an MP-CEM (thus, both the first CEM and the second CEM are MP-CEMs).

The device comprising the bead beating system can be used to isolate intracellular biomolecules, including, but not limited to, DNA, RNA, and proteins, and/or to isolate or harvest bacterial metabolites including, for example, biodiesels, bioplastics, antibiotics, and antibodies. The method can further comprise isolating a bacterial protein and/or a bacterial nucleic acid (for example, RNA) from the lysate.

The devices described herein can be used in methods of concentrating particles or cells from a sample fluid. Thus, the invention encompasses a method for concentrating particles (e.g., negatively charged particles) from a sample fluid comprising introducing the sample fluid into the device described herein via the inlet conduit, inducing an electric field across the main chamber, and causing the sample fluid to flow first across the first CEM and then across the second CEM, wherein the particles are concentrated at the microporous structure. Negatively charged particles include cells, for example, bacterial cells, and viruses. In some embodiments, the voltage applied is between 50 mV and 500 V. In additional aspects, the flow rate is greater than about 0.1 ml/min. In further aspects, the flow rate is between about 0.1 ml/min to about 5 ml/min. The size of the main chamber and thus the CEMs can be scaled depending on the desired flow rate. As discussed above, the devices and methods described herein can separate low abundance particles (particles present at a low concentration in the sample fluid) from a large volume of sample fluid. The volume of sample fluid can, for example, be greater than about 0.1 ml. The volume of sample fluid will depend on the type of sample fluid and the method. For example, when the sample fluid is blood, the volume of sample fluid introduced into the device can be greater than or equal to about 0.5 ml, greater than or equal to about 1 ml, greater than or equal to about 4 ml, greater than or equal to about 5 ml, greater than or equal to about 10 ml, greater than or equal to about 100 ml, or greater than or equal to about 500 ml. As shown in the FIG. 3, the flow rate is proportional to the electric field in the ion depletion region. In addition, the charge variance of particles also affects the above mentioned relationship; for example, particles with lower charge need a higher electric field under the same flow rate.

In certain aspects, the electrokinetic concentration can occur over a course of minutes, or in another embodiment, can occur and/or be maintained for several hours, for example three, two, or 1.5 hours. As will be understood, conditions which can affect the concentration of the particles include time required for concentration of the particles, and/or the concentration factor include the dimensions of the device (e.g., the dimensions of the main chamber), the voltage applied, salt concentration of the liquid, pH of the liquid, and/or combination thereof.

In additional aspects, the electrokinetic concentrator can further comprise at least one waste reservoir in fluid communication with the cathodic side of the main chamber. The fluid remaining after concentration of the particles can be collected in the waste reservoir.

In certain aspects, the electrokinetic concentrator or components thereof are disposable. In yet other aspects, the electrokinetic concentrator or components thereof are reusable. In yet further aspects, the concentrator can have a sample loading capacity of 1 to about 50,000 individual fluid samples. In certain additional aspects, the concentrator is encased in a suitable housing, such as plastic, to provide a convenient and commercially-ready cartridge or cassette. In one embodiment, the concentrator will have suitable features on or in the housing for inserting, guiding, and aligning the device, such that, for example, a sample loading compartment is aligned with a reservoir in another device, which is to be coupled to the concentrator. For example, the concentrator may be equipped with insertion slots, tracks, or a combination thereof, or other adaptations for automation of the concentration process via a device of this invention. The concentrator can also be adapted, in one embodiment, for high throughput screening of multiple samples, such as will be useful in proteomics applications, as will be appreciated by one skilled in the art.

The device of the present invention can also comprise an array or plurality of the electrokinetic concentrators.

The concentration efficiency of the device can be determined, for example, using labeled particles, introduced into the concentrator in known ratios and detecting the concentrated labeled particles. Signal intensity can be determined as a function of time, over background noise. In additional aspects, the concentrators described herein can be used under controlled physicochemical parameters, which may comprise temperature, pH, salt concentration, or a combination thereof. In certain aspects, the device comprises a downstream separation device including, but are not limited to, micro high performance liquid chromatographic columns, for example, reverse-phase, ion-exchange, and affinity columns.

In certain aspects, the electrokinetic concentrator or method described herein comprises a system or incorporates an assay such that analysis or measurement of the particles or lysate can be conducted. In certain preferred embodiments, the system or assay for analysis and/or measurement of the concentrated particles is downstream or occurs downstream of the concentrator. The system or assay means can, for example, be an instrument, component or assay selected from the group consisting of polymerase chain reaction (PCR), quantitative PCR (qPCR), reverse transcriptase PCR (RT-PCR), nucleic acid sequence based amplification (NASBA), loop mediated isothermal amplification (LAMP), rolling circle amplification (RCA), high-throughput bacteriophage-based sensor, immunoassay, immunoPCR (iPCR), enzyme activity assay, staining, imaging, whole genome amplification (WGA), in situ PCR, in situ WGA, polony formation, sequencing, single-molecule sequencing, nanopore analysis, nanopore sequencing, single-molecule imaging, DNA ball formation, electrophoresis, microelectromechanical systems (MEMS) electrophoresis, mass spectrometry, chromatography (e.g., HPLC), proximity ligation assay, electrochemical detection, plasmon resonance (SPR), hybridization assay (e.g., in situ hybridization assay such as fluorescence in situ hybridization (FISH)) FRET, cell sorting (e.g., FACS), electrochemiluminescence ELISA, and chemiluminescence ELISA. In yet additional aspects, the system or method comprises an immunochromatography sensor, such as a test strip. Lateral flow test strips are well-known in the art. In exemplary embodiments, test sample is added to the test surface, typically followed by a chase buffer. The chase buffer facilitates the flow of fluids across the test surface. The test strip also contains a labelled antibody, such as gold particles attached to antibodies. The analyte (the concentrated particle or a component thereof) present in the sample can bind to the labeled antibodies and the complex migrates through the membrane by capillary action. The analyte and label complex can then bind to antibodies which are immobilized on the membrane, creating a detectable indicator, such as a colored line, in the test zone. If no analyte is present in the sample, then the conjugate migrates past the test zone and will not bind to the antibodies on the test line of the membrane. In certain aspects, the immunochromatographic sensor or method comprises: (1) contacting the concentrated particles with a test strip having a first part retaining a labeled first antibody with affinity for the particle, or the specific substance that is labeled, a second part disposed downstream from the first part, on which a second antibody directed to the particle is immobilized, and (2) obtaining a detectable signal of the label at the second part or a part existing downstream therefrom. It is to be understood that the exact configuration of any systems, devices, etc. which are coupled downstream of the concentrating device are to be considered as part of this invention, and that the configuration can be varied, to suit a desired application.

Figures 7A, 7B, 7C, 7D, 7E, 7F, 7G:
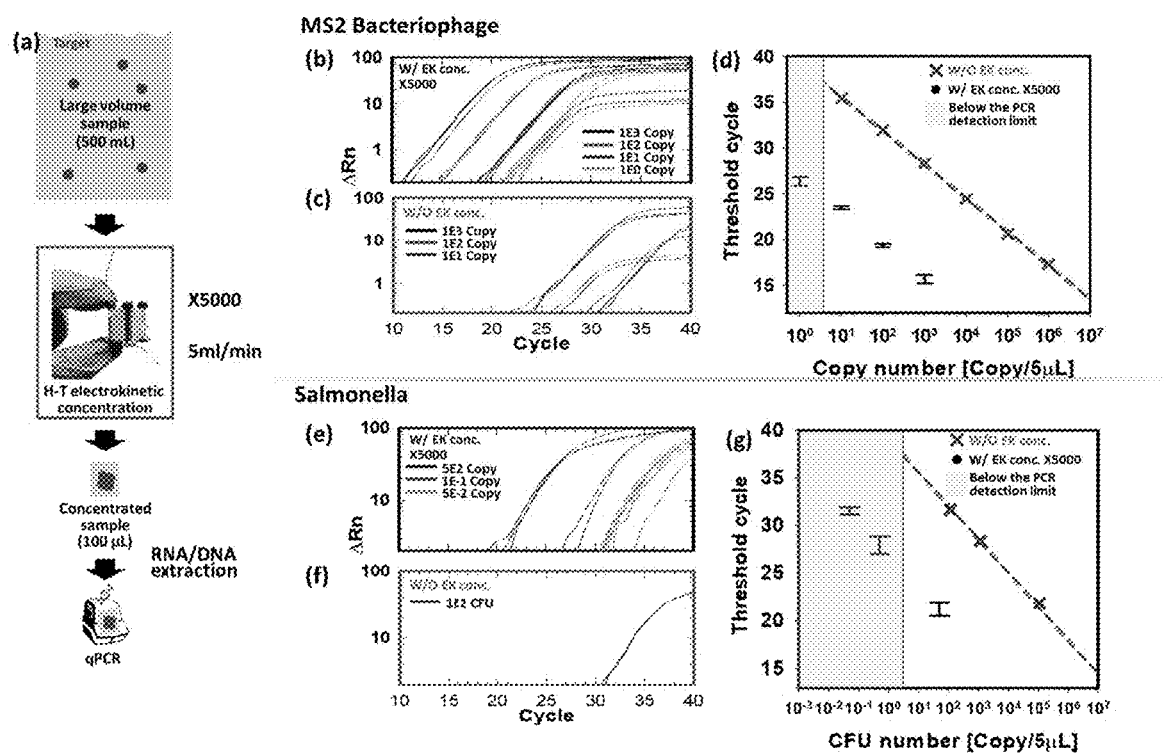
FIG. 7A shows the experimental setup for the performance evaluation of the electrokinetic concentrator using the downstream qPCR. A known quantity of target pathogen was spiked-in into the 500 mL of water. Using the electrokinetic concentrator, it was concentrated down to 100 uL (X5000) at a flow rate of 5 mL/min.
FIGS. 7B-7D shows the results of the virus (MS2 bacteriophage) detection with or without the proposed electrokinetic (EK) concentrator for comparison. The virus can be detected at a concentration even less than the RT-qPCR detection limit (1 PFU/5 ul). Note that the lower threshold cycle means higher viral RNA concentration.
FIGS. 7E to 7G shows qPCR results of the bacteria (*Salmonella*) detection with or without the proposed electrokinetic concentrator for comparison. The bacteria can be detected at a concentration even less than the RT-qPCR detection limit (0.1, 1 CFU/5 ul).

The devices and methods described herein can be used for various different applications, for example, where concentration and/or detection of a low amount or concentration (low abundance) of cell, bacteria, virus, fungi, or other particle in a sample fluid is desirable. For example, the devices and methods can be used for the detection of low abundance bacteria or low abundance virus from a biological sample by selectively concentrating the low abundance bacteria or low abundance and virus using the devices and methods described herein, and optionally, detecting or measuring the bacteria or virus using a downstream assay, sensor or instrument. For example, sepsis, a major cause of mortality, can be caused by low abundant bacteria. In order to provide effective treatment for sepsis in hospital settings, fast diagnosis is needed. However, the current method antimicrobial susceptibility testing (AST) is too slow to affect initial treatment decisions in the early stages of sepsis (Inglis et al. (2019), J Med Microbiol 68(7): 973-977). Detection method for low abundance bacteria or virus in the blood is challenging because of the large amount/concentration of the background components including, but not limited to, red blood cells, white blood cells, and platelets. The device and method described herein permit selective bacteria or virus concentration in a manner that is free of the clogging issue that would be observed using a conventional filter. Thus, the devices and methods can be used as a pre-concentrator for fast and reliable bacteria or virus detection, including, for example, when the initial concentration in the sample fluid is below the level of detection for a specific downstream assay or sensor. Various downstream assays or instruments could be used for the detection of specific bacteria or virus in the sample. In certain aspects, the low abundance bacteria is present in the sample at a concentration of 200 colony-forming units/ml of biological sample or less, for example, as shown in FIGS. 7A and 7B.

The invention encompasses a method for the diagnosis of sepsis comprising the step of concentrating bacteria from a blood sample using the device described herein; for example, the bacteria to be concentrated can be gram-negative bacteria which produce endotoxin, which is also known as lipopolysaccharide (LPS). LPS is the most common gram-negative bacterial trigger of cytokine release or gram-positive which produce lipoteichoic acid, peptidoglycan, hemolysins (cytolysins) and superantigens. Specific bacteria which can be concentrated include, for example, *Escherichia coli, Klebsiella pneumoniae, Enterobacter, Pseudomonas aeruginosa, Proteus, Bacteroides fragilis, Streptococcus pneumoniae, Streptococcus pyogenes, Staphylococcus aureus*, or *Enterococcus*.

Figures 8A, 8B, 8C:
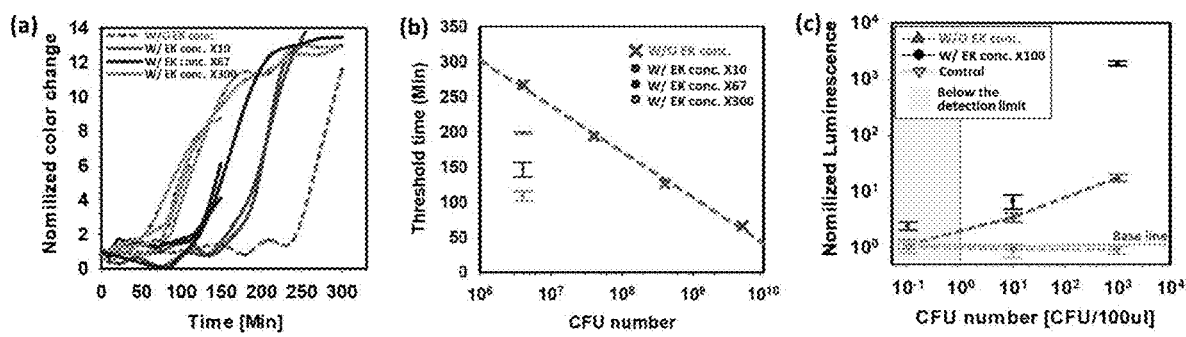
FIGS. 8A-8C shows that by using the SAMPLE6 (high-throughput bacteriophage-based sensor) with electrokinetic concentration (up to X100), *Salmonella* can be detected at a concentration even below the detection limit (0.1 CFU/100 ul). The result also indicates availability of culture-based detection because bacteria is intact.

In additional aspects, the method is directed to the detection of virus or low abundance virus from a sample, such as a blood sample. In certain aspects, the virus is selected from the group consisting of influenza, RSV, coronavirus (including for example, SARS-CoV and SARS-CoV-2/COVID-19), Zika virus, Dengue virus, and Chikungunya virus. In yet further aspects, the method is for detection of virus and the downstream assay is PCR or RT-PCR. Such a method is exemplified in FIG. 8A-8C.

In yet further aspects, the method is directed to the detection of bacteria, virus or other biomolecules in a CSF sample. Such methods can, for example, be used to diagnose meningitis. Meningitis, including bacterial and viral meningitis, is an inflammation of the membranes surrounding the brain and spinal cord. Most forms of meningitis are caused by a viral, bacterial, or fungal infection of the cerebrospinal fluid (CSF). In order to diagnosis meningitis, a series of laboratory tests need to be performed and these tests entail sample preparation for detection of each virus, bacteria, and fungi. For example, detection of low abundant bacteria can be accomplished by culture but some bacteria, such as Mycobacterium tuberculosis, need six weeks for positive identification. With respect to low abundant viruses, these cannot be concentrated by conventional centrifugation methods due to the size of the virus. As such, meningitis diagnosis tests process usually takes more than 48 hours. Outcomes are improved by fast and reliable diagnosis. Thus, the invention encompasses a method of concentrating bacteria, virus, or fungi from a CSF sample of a patient suspected of suffering from meningitis using the devices and methods described herein. The inventive devices and methods allow one-step sample preparation for the pathogen identification.

The devices and methods described herein can also be used to detect bacterial contamination in food. Bacterial contamination and infection is a significant problem in the food industry. The detection of individual cells in large volumes poses a major challenge for existing detection technologies. In order to overcome these hurdles, current methods for bacterial pathogen detection rely on an enrichment step (or steps) based on cell culture to increase the number of target pathogen cells. Enrichment is necessarily an imperfect and slow process (for example, enrichment can take 8 to 48 hours depending on the bacterial target and background microflora). Thus, current diagnostics for food pathogens impose a large time lag between sampling and final results, during which time the sampled conditions may have changed such that the ultimate results of the assay cannot be confidently utilized to remediate contamination in already widely distributed food products. Thus, there is a strong need for rapid concentration in food monitoring, which is certainly recognized by the industry but also demanded by government, for example, via the FDA Food Safety Challenge and the Food Modernization Safety Act. The devices and methods described herein can concentrate a pathogen from a large volume/amount of sample quickly (e.g, 200 ml concentration in 20 mins) without any cell culturing and thus allows rapid monitoring of food contamination.

Figures 9A, 9B, 9C, 9D:
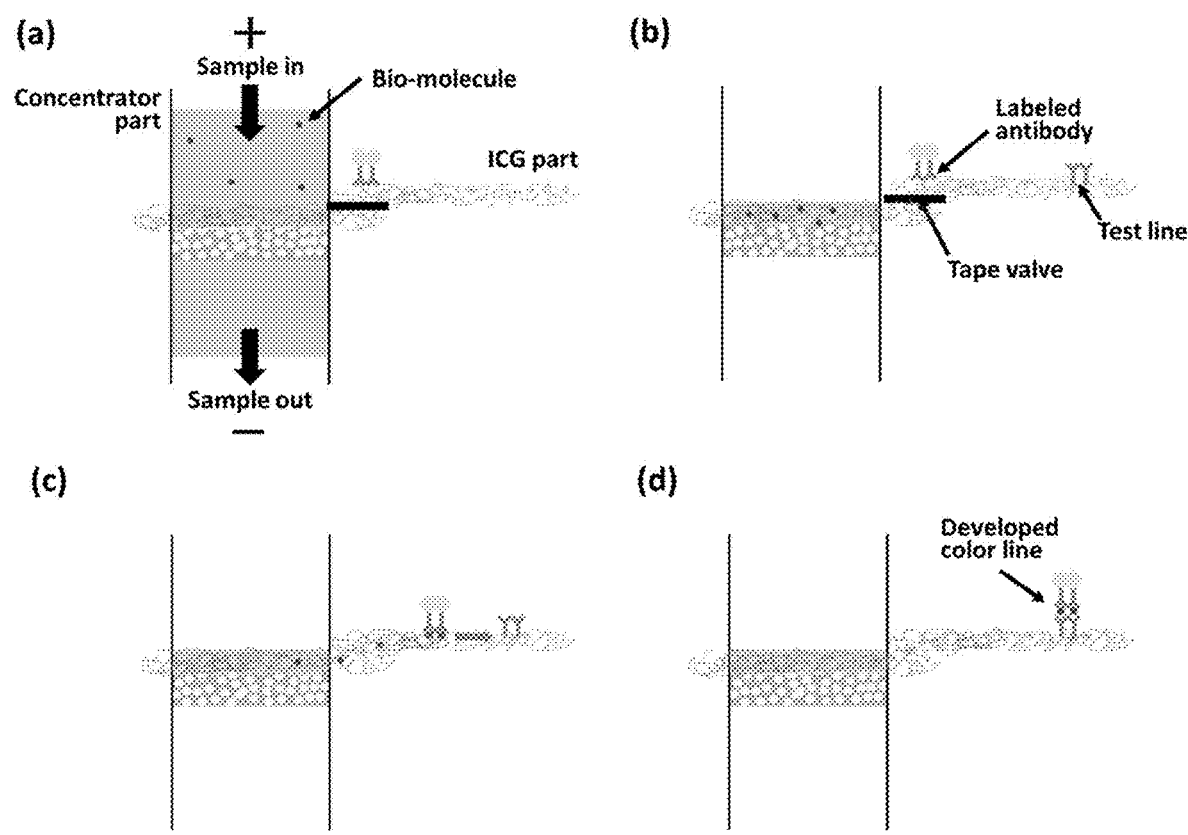
FIGS. 9A-9D shows integration of the electrokinetic concentration device with a strip sensor (Immunochromatography, ICG) as a downstream detection assay.

The devices and methods described herein can also be used for the detection of waterborne pathogens. There is a large unmet need for technologies that can provide quick and sensitive detection of waterborne pathogens for human health. For example, it would be useful if low abundant virus, such as Norovirus or Poliovirus, could be detected. Conventionally, a filtration membrane is used for collecting and sieving the virus [6], yet these methods are not reliable because of clogging issues, substantial pressure requirements, and generally low flow-rate [7]. In order to reduce the clogging issue, a filter having a large surface area has been used. However, the large surface area of the filter limits concentration efficiency. The proposed technology uses electrophoretic force, instead of sieving by the filter, that can concentrate charged water contaminants in a fast and high-throughput manner. In addition, the electrokinetic concentrator described herein strikes a balance between cost and sensitivity, by enabling the meaningful detection of bacteria, virus, or heavy metal ion even with low-sensitivity and low-cost sensors such as paper strip test as shown in FIG. 9.

The devices and methods described herein can also be used to detect contamination in biomanufacturing process. Biomanufacturing uses biological systems to construct or prepare biomaterials including, but not limited to, amino acids, vaccines, cytokines, fusion proteins, growth factors, biopharmaceuticals, and antibodies (e.g., monoclonal antibodies). Detection of microbiological contamination critical in such biomanufacturing processes, especially for the batched cell culture process. For example, in 2010, a pediatric rotavirus vaccine was found to be contaminated with porcine circovirus and, as a result, health authorities recommended suspension of it use for a period of time.

REFERENCES

[1] Kwak, R., Kim, S. J. & Han, J. Continuous-flow biomolecule and cell concentrator by ion concentration polarization. *Anal. Chem.* 83, 7348-55 (2011).
[2] Wang, Y.-C., Stevens, A. L. & Han, J. Million-fold preconcentration of proteins and peptides by nanofluidic filter. *Anal. Chem.* 77, 4293-9 (2005).
[3] Ouyang, W., Li, Z. & Han, J. Pressure-Modulated Selective Electrokinetic Trapping for Direct Enrichment, Purification, and Detection of Nucleic Acids in Human Serum. *Anal. Chem.* 90, 11366-11375 (2018).
[4] Pham, S. V. et al. Helical vortex formation in three-dimensional electrochemical systems with ion-selective membranes. *Phys. Rev. E* 93, 033114 (2016).

[5] Kwon, H. J., Kim, B., Lim, G. & Han, J. A multiscale-pore ion exchange membrane for better energy efficiency. *J. Mater. Chem. A* 6, 7714-7723 (2018).

[6] Fout, G. S., Cashdollar, J. L., Varughese, E. A., Parshionikar, S. U. & Grimm, A. C. EPA Method 1615. Measurement of enterovirus and norovirus occurrence in water by culture and RT-qPCR. I. Collection of virus samples. *J Vis Exp* 1-7 (2015). doi:10.3791/52067

[7] Cashdollar, J. L. & Wymer, L. Methods for primary concentration of viruses from water samples: A review and meta-analysis of recent studies. *J. Appl. Microbiol.* 115, 1-11 (2013).

All references, articles, patent applications, patent publications and patents are incorporated herein by reference in their entirety. While this invention has been particularly shown and described with references to preferred embodiments thereof, it will be understood by those skilled in the art that various changes in form and details may be made therein without departing from the scope of the invention encompassed by the appended claims.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

What is claimed is:

1. An electrokinetic concentrating device comprising:
   i) a liquid source comprising a sample liquid comprising negatively charged biological particles;
   ii) an anode chamber comprising an anode and a buffer solution;
   iii) a cathode chamber comprising a cathode and a buffer solution;
   iv) a main chamber disposed between the anode chamber and the cathode chamber and separated therefrom, wherein the main chamber further comprises a first CEM on the anodic side of the main chamber and a second CEM on the cathodic side of the main chamber, wherein the second CEM is a multi-scale porous cation exchange membrane (a MP-CEM), and wherein the first CEM and the second CEM are configured in the main chamber such that the sample liquid flows across the first CEM and then across the second CEM;
   v) a microporous structure disposed on or in proximity to the second CEM between the first CEM and the second CEM in the main chamber, wherein the microporous structure is closer to the second CEM than it is to the first CEM, and wherein the microporous structure suppresses electroconvection; and
   vi) an inlet conduit in fluid communication with the liquid source and with the anodic side of the main chamber and configured to direct a flow of the sample liquid to the anodic side of the main chamber such that the sample liquid flows across the first CEM, then through the microporous structure, and then through the second CEM;
   wherein the anode, the cathode, and the second CEM are configured to induce an electric field and an ion-depleted region in the main chamber in which the negatively charged biological particles from the sample liquid are concentrated; wherein the MP-CEM comprises nanopores and micropores; wherein the microporous structure is disposed on or in proximity to the top side of the second CEM and stabilizes the ion-depleted region on the second CEM.

2. The device of claim 1, wherein the first CEM does not comprise micropores.

3. The device of claim 1, wherein the micropores of the MP-CEM have a diameter of about 50 to about 300 um.

4. The device of claim 1, wherein the first CEM is an MP-CEM.

5. The device of claim 1, wherein the negatively charged biological particles are concentrated at the microporous structure.

6. The device of claim 1, wherein the microporous structure is made from fibers.

7. The device of claim 1, wherein the microporous structure is a cotton ball.

8. The device of claim 1, wherein the microporous structure is a plurality of beads.

9. The device of claim 8, wherein the plurality of beads is part of a bead beating system.

10. The device of claim 8, wherein the diameter of the beads is between 50 to 300 um.

11. The device of claim 8, wherein the beads are packed such that their porosity is between about 10 and about 40%.

12. The device of claim 9, wherein the bead beading system comprises the plurality of beads packed between a porous membrane and mesh.

13. The device of claim 12, wherein the porous membrane is porous PDMS.

14. The device of claim 8, wherein the first CEM is an MP-CEM.

15. The device of claim 1, wherein the microporous structure has a height of at least about 1 mm.

16. The device of claim 5, further comprising a sensor or instrument for detecting and/or measuring the concentrated negatively charged biological particles.

17. The device of claim 16, wherein the sensor is PCR or RT-PCR or a test strip.

18. A method for concentrating negatively charged biological particles from a sample liquid, the method comprising introducing the sample liquid into the device of claim 1 via the inlet conduit, inducing an electric field across the main chamber, and causing the sample liquid to flow first across the first CEM and then across the second CEM, wherein the negatively charged biological particles are concentrated at the microporous structure.

19. The method of claim 18, wherein the negatively charged biological particles are cells.

20. The method of claim 18, wherein the sample liquid is a biological fluid.

21. The method of claim 18, wherein the particles comprise proteins, polypeptides, nucleic acids, viral particles, or combinations thereof.

22. The method of claim 18, wherein the volume of sample liquid introduced into the device is greater than about 1 ml.

23. The method of claim 22, wherein the volume of sample liquid introduced into the device is greater than about 5 ml.

24. The method of claim 18, wherein said device is coupled to a separation system, a detection system, an analysis system or a combination thereof.

25. The method of claim 18, wherein PCR or RT-PCR of the concentrated negatively charged biological particles is conducted.

26. The method of claim 18, wherein the concentrated negatively charged biological particles are analyzed by immunochromatography.

27. The method of claim 18, wherein the flow rate of the sample liquid in the device is at least about 1 ml/min.

28. The method of claim 18, wherein the electric field is induced by applying a voltage, and wherein the voltage applied is between about 50 mV and 500 V.

29. A method for the detection of low abundance bacteria or low abundance virus in a sample liquid comprising the method of claim 18, wherein the particles are the low abundance bacteria or virus.

30. A method of diagnosing sepsis in a subject in need thereof comprising the method of claim 18, wherein the sample liquid is blood obtained from the subject, and the negatively charged biological particles are bacteria that cause sepsis.

31. A method for diagnosis of meningitis in a subject in need thereof comprising the method of claim 18, wherein the sample liquid is cerebrospinal fluid obtained from the subject, and the negatively charged biological particles are meningitis-causing bacteria, virus or fungi.

32. A method of monitoring food safety comprising the method of claim 29.

33. A method of detection of waterborne pathogen comprising the method of claim 29.

* * * * *